(12) United States Patent
Sinha et al.

(10) Patent No.: US 10,105,049 B2
(45) Date of Patent: Oct. 23, 2018

(54) METHODS AND APPARATUS FOR ANTERIOR SEGMENT OCULAR IMAGING

(71) Applicants: Massachusetts Institute of Technology, Cambridge, MA (US); Vincent Patalano, II, Winchester, MA (US)

(72) Inventors: Shantanu Sinha, Boston, MA (US); Hyunsung Park, Cambridge, MA (US); Albert Redo-Sanchez, Cambridge, MA (US); Matthew Everett Lawson, Winthrop, MA (US); Nickolaos Savidis, Watertown, MA (US); Pushyami Rachapudi, Hyderabad (IN); Ramesh Raskar, Cambridge, MA (US); Vincent Patalano, II, Winchester, MA (US)

(*) Notice: Subject to any disclaimer, the term of this patent is extended or adjusted under 35 U.S.C. 154(b) by 11 days.

(21) Appl. No.: 15/000,032

(22) Filed: Jan. 19, 2016

(65) Prior Publication Data
US 2016/0206197 A1    Jul. 21, 2016

Related U.S. Application Data

(60) Provisional application No. 62/145,364, filed on Apr. 9, 2015, provisional application No. 62/104,505, filed on Jan. 16, 2015.

(51) Int. Cl.
*A61B 3/00* (2006.01)
*A61B 3/10* (2006.01)
(Continued)

(52) U.S. Cl.
CPC ............ *A61B 3/117* (2013.01); *A61B 3/0025* (2013.01); *A61B 3/1025* (2013.01); *A61B 3/14* (2013.01); *G02B 5/10* (2013.01)

(58) Field of Classification Search
CPC ..... A61B 3/117; A61B 3/0025; A61B 3/1025; A61B 3/14; G02B 5/10
(Continued)

(56) References Cited

U.S. PATENT DOCUMENTS 6,599,285 B1    7/2003    Lieberman et al.
6,758,564 B2    7/2004    Ferguson
(Continued)

FOREIGN PATENT DOCUMENTS

WO    2013152205 A1    10/2013
WO    2015018514 A1    2/2015

OTHER PUBLICATIONS

Berard, P., et al., High-quality capture of eyes; published in ACM Transactions on Graphics (TOG)—Proceedings of ACM SIG-GRAPH Asia 2014, vol. 33, Issue 6, Nov. 2014, Article No. 223, ACM New York, NY, USA.
(Continued)

*Primary Examiner* — Jie Lei
*Assistant Examiner* — Mitchell Oestreich
(74) *Attorney, Agent, or Firm* — Stephen R. Otis

(57) ABSTRACT

A projector and one or more optical components project a light pattern that scans at least a portion of an anterior segment of an eye of a user, while one or more cameras capture images of the anterior segment. During each scan, different pixels in the projector emit light at different times, causing the light pattern to repeatedly change orientation relative to the eye and thus to illuminate multiple different cross-sections of the anterior segment. The cameras capture images of each cross-section from a total of at least two different vantage points relative to the head of the user. The position of the projector, optical components and cameras relative to the head of the user remains substantially constant throughout each entire scan.

20 Claims, 12 Drawing Sheets

(51) Int. Cl.
*A61B 3/117* (2006.01)
*G02B 5/10* (2006.01)
*A61B 3/14* (2006.01)

(58) Field of Classification Search
USPC ........................................................ 351/206
See application file for complete search history.

(56) References Cited

U.S. PATENT DOCUMENTS

| | | | |
|---|---|---|---|
| 6,789,908 B2 | 9/2004 | Garcia | |
| 7,264,355 B2* | 9/2007 | Rathjen | ................ A61B 3/1005 |
| | | | 351/206 |
| 7,275,826 B2 | 10/2007 | Liang | |
| 7,431,459 B2 | 10/2008 | Somani | |
| 7,736,003 B2 | 6/2010 | Lieberman et al. | |
| 7,831,106 B2 | 11/2010 | Elsner et al. | |
| 8,070,289 B2 | 12/2011 | Peyman | |
| 2004/0109401 A1* | 6/2004 | Ogasawara | .......... G11B 7/1275 |
| | | | 369/112.19 |
| 2008/0151185 A1* | 6/2008 | Saito | ........................ A61B 3/12 |
| | | | 351/206 |
| 2013/0107208 A1 | 5/2013 | Endo et al. | |
| 2014/0218689 A1* | 8/2014 | Heitel | ..................... A61F 9/008 |
| | | | 351/221 |

OTHER PUBLICATIONS

Jain, R., Pentacam: Principle and Clinical Applications; published in Journal of Current Glaucoma Practice, May-Aug. 2009;3(2): 20-32.

Santi, P., Light sheet fluorescence microscopy: a review; published in Journal of Histochemistry & Cytochemistry, Feb. 2011; 59(2):129-38.

* cited by examiner

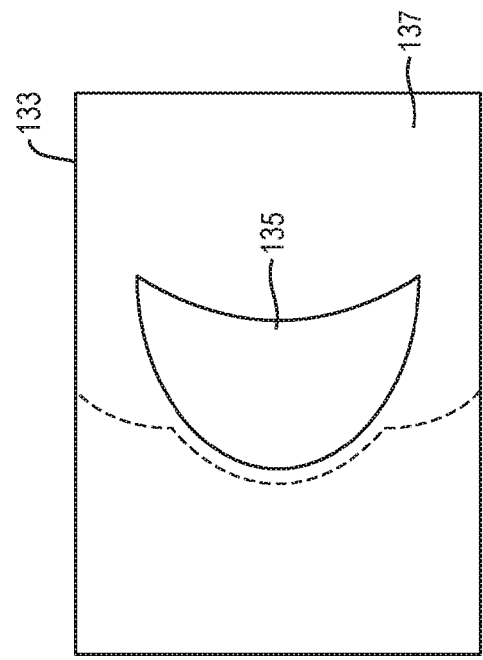
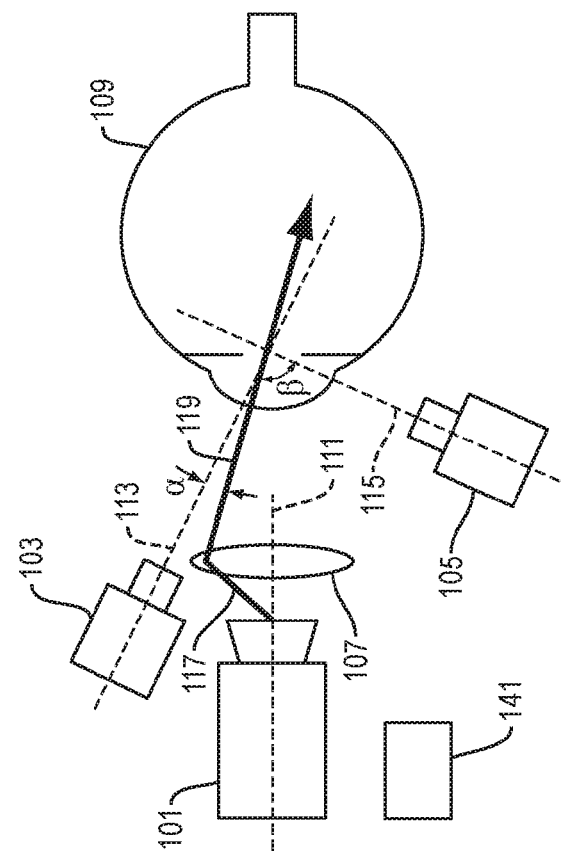
FIG. 1B
FIG. 1A

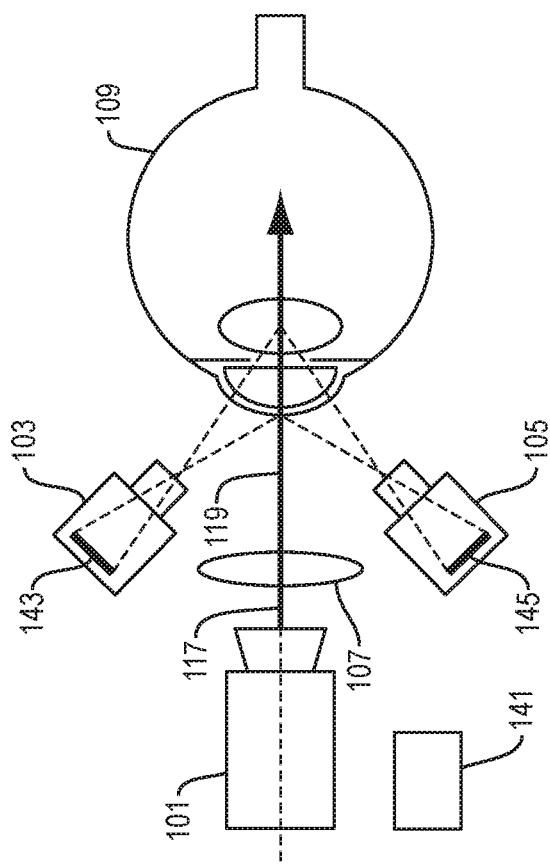
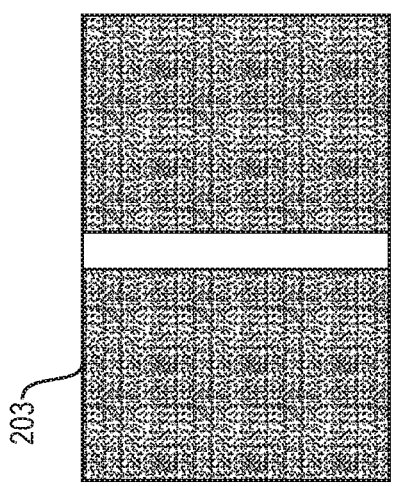

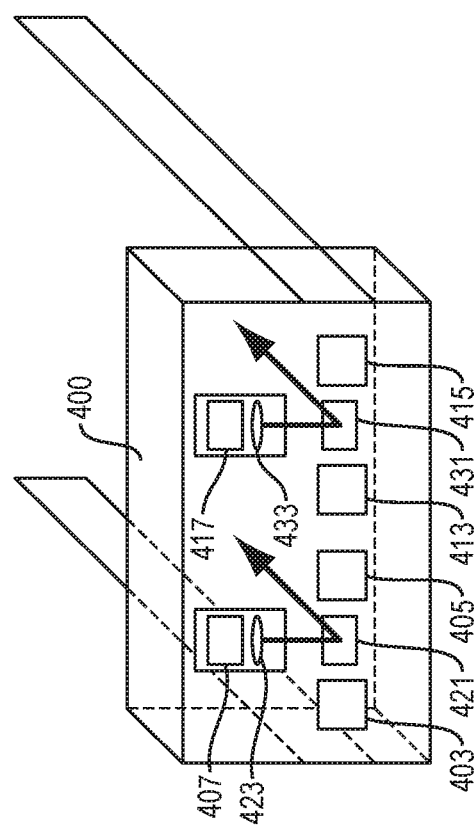
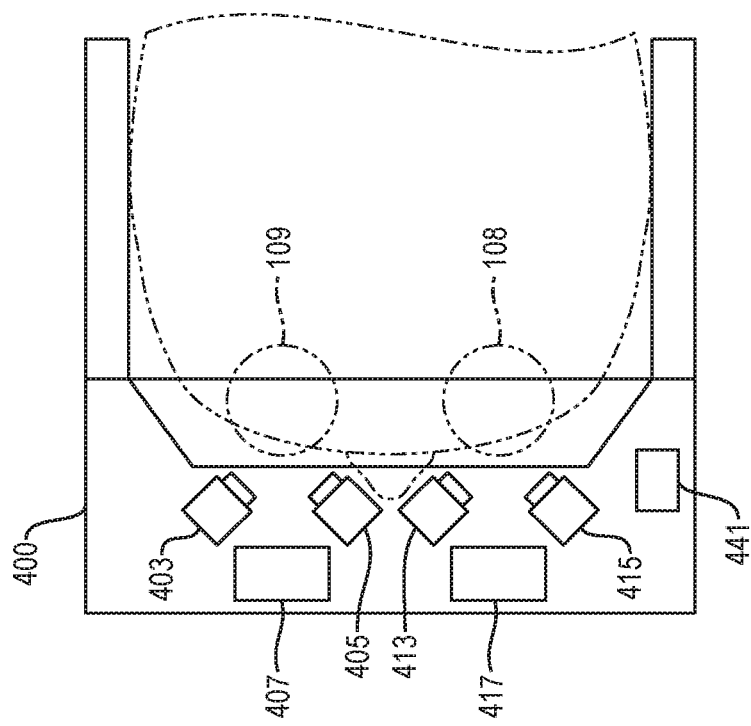

METHODS AND APPARATUS FOR ANTERIOR SEGMENT OCULAR IMAGING

RELATED APPLICATIONS

This application is a non-provisional of, and claims the benefit of the filing date of, U.S. Provisional Patent Application No. 62/104,505 filed Jan. 16, 2015 (the "505 Application"), and U.S. Provisional Patent Application No. 62/145,364 filed Apr. 9, 2015 (the "364 Application). The entire disclosures of the 505 Application and the 364 Application are incorporated herein by reference.

FIELD OF TECHNOLOGY

The present invention relates generally to capturing images of the anterior segment of the eye and based, on the images, reconstructing 3D shape of structures in the anterior segment.

BACKGROUND

The human eye has two principal anatomical segments: the anterior segment and the posterior segment. The anterior segment includes the cornea, iris, lens, ciliary body, and the anterior portion of the sclera. It also includes the anterior chamber, which lies between the cornea and the iris, and the posterior chamber, which lies between the iris and the lens. Both the anterior and posterior chambers are filled with aqueous humor.

Many disorders, such as cataracts, ulcers, pterygia, and angle-closure glaucomas affect the anterior segment of the eye and can lead to blindness if left undiagnosed.

The conventional "gold standard" for screening the anterior segment of the eye is the ophthalmic slit lamp. A slit lamp comprises a high-intensity light source that may be focused to shine a thin sheet of light into the eye. Different layers of the anterior segment have different refractive indices, resulting in the scattering of light at the boundary of these layers. This sheet of light illuminates a thin slice of the eye that, when viewed at a sufficiently large angle off the optical axis of illumination, allows for viewing of a cross-sectional view of the anterior segment. Manipulation of the angle at which this sheet of light hits the surface of the eye allows for viewing different cross-sections of the eye. Various pathologies and conditions affecting the anterior segment manifest themselves as a change in refractive index and scattering properties.

The need for mechanically rotating arms to manipulate the light sheet and eyepiece constrains the form factor and size of the conventional slit lamp. A shorter arm length would result in a lower tolerance for error in position of the end of the arm, making it harder to illuminate the desired cross-section of the eye. Additionally, the presence of moving parts requires the device to be sufficiently far from the subject's eye to prevent injury.

SUMMARY

In illustrative implementations of this invention, a low-cost, wearable solid-state device with no moving optical parts is used to create a full 3D reconstruction of the anterior segment of the eye (including the corneal epithelium and endothelium, the iris, the pupil and the crystalline lens). A pico-projector projects computationally generated patterns onto the eye and one or more cameras image the scattering produced at the boundary of optical media with different refractive indices. A computer executes a software program to reconstruct a 3D model of the anterior segment of the eye. The computer uses the generated 3D model to produce topographical maps of the anterior and posterior surfaces of the cornea, measure the curvature at any point of the cornea and to measure corneal thickness.

In illustrative implementations, an internal feedback loop between the illumination and imaging allows the entire data capture process to proceed automatically and rapidly (e.g., in less than 5 seconds or in less than 2 seconds). The data capture process does not require the presence of a trained optical professional In some implementations, the imaging system is housed in a head-mounted device for automated screening of the anterior segment of the eye.

In some implementations of this invention, a scanning light sheet is projected onto an eye without using any moving optical parts, while a system of cameras images individual cross-sections of the anterior segment of the eye.

In illustrative implementations, a projector and one or more optical components project a light pattern that scans at least a portion of an anterior segment of an eye of a user, while one or more cameras capture images of the anterior segment. During each scan, different pixels in the projector emit light at different times, causing the light pattern to repeatedly change orientation relative to the eye and thus to illuminate multiple different cross-sections of the anterior segment. The one or more cameras capture the images of each cross-section from a total of at least two different vantage points relative to the head of the user. The position of the one or more cameras, the projector and the one or more optical components relative to the head of the user remains substantially constant throughout each entire scan.

The description of the present invention in the Summary and Abstract sections hereof is just a summary. It is intended only to give a general introduction to some illustrative implementations of this invention. It does not describe all of the details and variations of this invention. Likewise, the descriptions of this invention in the Field of Technology section is not limiting; instead it identifies, in a general, non-exclusive manner, a technology to which exemplary implementations of this invention generally relate. Likewise, the Title of this document does not limit the invention in any way; instead the Title is merely a general, non-exclusive way of referring to this invention. This invention may be implemented in many other ways.

BRIEF DESCRIPTION OF THE DRAWINGS

FIGS. 1A to 1D show an anterior segment of an eye being imaged from different vantage points. FIG. 1A shows two cameras, each at a different vantage point. FIG. 1B shows an image of a cross-section of the anterior segment, captured by a camera at a large angle relative to a sheet of light illuminating the anterior segment. FIG. 1C shows an image of a cross-section of the anterior segment, captured by a camera at a narrow angle relative to the sheet of light illuminating the anterior segment. FIG. 1D illustrates that the smaller the viewing angle, the smaller the image sensor region that captures an image of the cross-section of the eye.

FIG. 2C shows a centered light pattern 201 displayed by a projector. FIG. 2D shows the projector projecting the centered light pattern while two cameras capture images.

FIG. 4A is a top view of a head-mounted device for anterior segment imaging.

FIG. 4B shows hardware in a head-mounted device for anterior segment imaging.

Figure 1D:
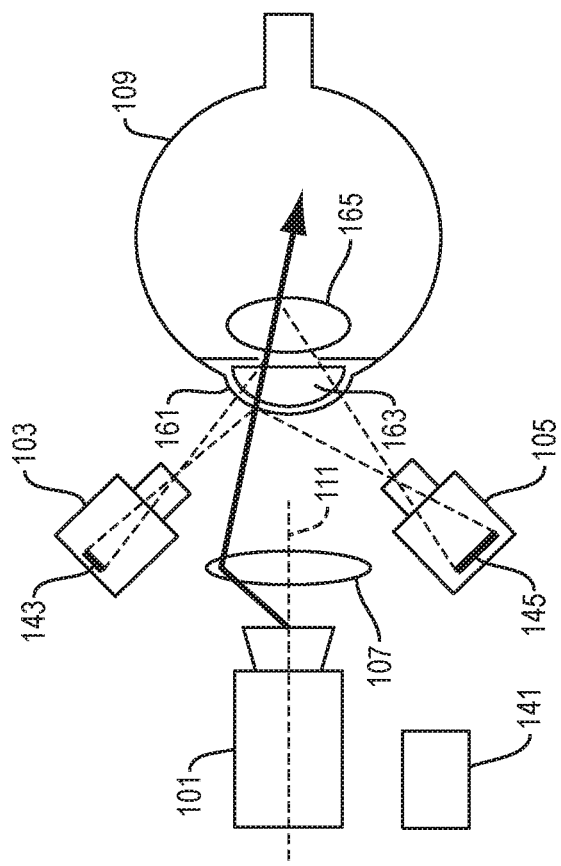

The above Figures show some illustrative implementations of this invention, or provide information that relates to those implementations. However, this invention may be implemented in many other ways.

DETAILED DESCRIPTION

Hardware, Generally

In illustrative implementations of this invention, an imaging system comprises a pico-projector, one or more cameras, one or more other optical components and one or more computers. A laser projector or an LED-based projector with a high contrast ratio creates a large difference in light intensity between pixels that are illuminated due to the projected pattern and those that are not.

In some implementations, two cameras image the eye from two different angles that are off-axis (that is, not parallel to the optical axis of the eye). The pico-projector projects patterns onto the surface of the eye through a system of optical components. In some implementations, these optical components include collimating and focusing optics.

The pico-projector projects any computationally generated pattern onto the eye. One such example is a moving slit—a moving straight line in the projector's frame of reference The width, orientation, direction of motion and scanning speed of this slit are controlled in software to present the camera system with a cross-sectional view of the anterior segment of the eye, produced due to scattering at boundaries between media with different refractive indices—such as the air-corneal epithelium boundary, epithelium-stroma boundary, or stroma-endothelium boundary.

The patterns projected by the projector are programmatically controlled and are, hence, known as a function of time. The geometry of the device—the relative positions of the cameras with respective to each other and to the projector and the distances between various optical components— does not change after initial manufacturing, and is hence known. When an eye is placed in front of the device, the images captured by the cameras are determined by (i) the pattern being projected by the projector at that time instant, (ii) the geometry of the device and (iii) the geometry of the eye. Since (i) and (ii) are completely specified, (iii) may be calculated based on the images captured.

For the more specific case of projection of a light sheet, only a thin cross-sectional slice of the object is illuminated at any given time and, hence, only this slice is imaged by the cameras at any given time. Each camera would thus, at any given time, image a cross-sectional slice of the anterior segment of the eye multiplied by a scaling factor related to the viewing angle of the camera (sine of the viewing angle) and the power of the camera lens. for a 90 degree viewing angle, this image would directly correspond to the slice being imaged, while for a 0 degree viewing angle only a line would be visible. As the sheet of light scans the anterior segment of the eye, different slices of the anterior segment are brought into view and imaged by the cameras. The exact orientation of each slice within the anterior segment is determined by (i) the pattern being projected and (ii) the optics between the projector and the object. Both (i) and (ii) are known a priori and, hence, the exact orientation of every slice may be computed. Given this information, a computer performs an algorithm that computationally stacks images in 3D space to reconstruct a 3D point cloud of a region of the anterior segment of the eye from a series of 2D images.

As used herein, the "viewing angle" of a camera, for an image of a cross-section of the anterior segment of the eye captured by the camera at a given time when the anterior segment is illuminated by a plane of light, means the minimum angle at the given time between (a) the plane of light and (b) the optical axis of the camera. In this context, the plane of light and the plane of cross-section are identical.

In illustrative implementations, the position of projector, cameras, and other optical components relative to the head of the user remains substantially constant throughout each entire scan.

Imaging From Multiple Vantage Points Simultaneously

In illustrative implementations of this invention, it is desirable to image the eye from at least two different vantage points simultaneously. For example, two cameras may be positioned such that they image the eye from different vantage points simultaneously. Alternatively, a single camera and mirror system may be used to image the image eye from different vantage points simultaneously, as discussed below.

FIGS. 1A to 1D show an anterior segment of an eye being imaged from different vantage points simultaneously, in illustrative implementations of this invention.

FIG. 1A shows two cameras 103, 105, each at a different vantage point relative to an eye 109. A pico-projector 101 projects light in direction 117. Then a lens 107 refracts the light, such that a plane of light 119 enters the eye 109.

In each of the Figures in which lens 107 occurs, lens 107 comprises any set of one or more lenses. In some cases, lens 107 is a single lens. In many other cases (such as the example shown in FIG. 9), lens 107 comprises a set of multiple lenses, including a collimating lens that collimates light for a portion of an optical path to the eye.

In the example shown in FIG. 1A: the viewing angle of camera 105 is angle $\beta$; angle $\beta$ is 90 degrees; and the scaling factor is sine $\beta=1$. Thus, in image 133 captured by camera 105, the cross-section appears full-sized and is not reduced by the scaling factor.

FIG. 1B shows this image 133—i.e., the image captured by camera 105 at viewing angle $\beta=90°$ shown in FIG. 1A. Image 133 is of a cross-section of an eye 137, including the anterior chamber 135 of the eye 137.

In the example shown in FIG. 1A, the viewing angle of camera 103 is angle α; angle α is approximately 20 degrees; and the scaling factor is sine α<1. Thus, in image 123 captured by camera 103, the cross-section appears thin and is reduced in width by the scaling factor.

Figure 1C:
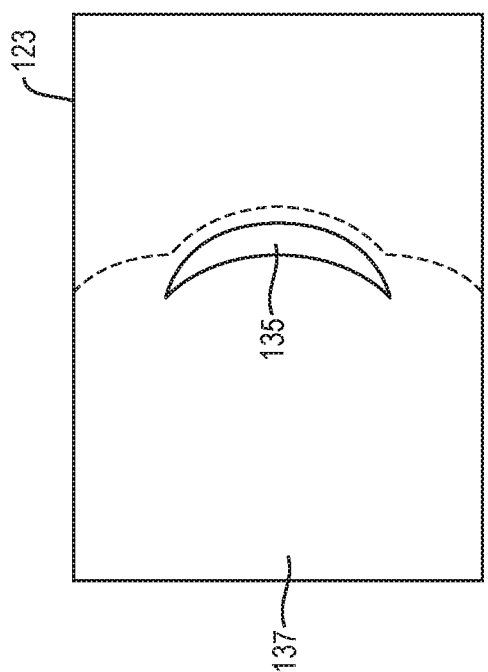

FIG. 1C shows this image 123—i.e., the image captured by camera 103 at viewing angle α=20° shown in FIG. 1A. Image 123 is of a cross-section of the eye 137, including the anterior chamber 135 of the eye 137.

Because image 123 was captured at a smaller viewing angle than image 133, the cross-section in image 123 appears thinner than in image 133.

In the example shown in FIG. 1A, the two cameras 103, 105 capture images 123, 133 simultaneously, from angles α and β, respectively.

Note that FIG. 1A shows the optical setup at a given time and a given orientation of plane of light 119.

During a complete scan of the eye, plane of light 119 changes orientation over time, and thus the viewing angles of the cameras change over time (because the viewing angles are relative to the plane of light 119).

During each complete scan of an eye: (a) at some orientations of plane of light 119, viewing angle α of camera 103 is greater than viewing angle β of camera 105; and (b) at other orientations of plane of light 119, viewing angle α of camera 103 is smaller than viewing angle β of camera 105. For example, at some orientations of plane of light 119: (a) viewing angle α of camera 103 is so small that the cross-section appears thin in an image captured by camera 103; and (b) viewing angle β of camera 105 is larger and thus the cross-section appears wider in an image captured by camera 105. At other orientations of plane of light 119: (a) viewing angle β of camera 105 is so small that the cross-section appears thinner in an image captured by camera 105; and (b) viewing angle α of camera 103 is larger and thus the cross-section appears wider in an image captured by camera 103.

Thus, imaging the eye from different vantage points ensures that, even though the orientation of the plane of light changes over the course of a scan, the viewing angle from at least one of the vantage points is always wide enough that an image of the cross-section may be captured in which the cross-section appears reasonably wide.

FIG. 1D illustrates that the smaller the viewing angle, the smaller the image sensor region that captures an image of the cross-section of the eye. In the example shown in FIG. 1D: (a) camera 103 is at a smaller viewing angle than camera 105; (b) the cross-section appears thinner in an image captured by camera 103 than in an image captured by camera 105; (c) an image of the cross-section occupies regions 143 and 145 of the image sensor of cameras 103, 105, respectively; and (d) region 143 is smaller than region 105. In the example shown in FIG. 1D, the cameras image the anterior segment of the eye, including the cornea 161, anterior chamber 163 and crystalline lens 165.

In the examples shown in FIGS. 1A, 1D, 2B, 2D, 5B, 5C, the plane of light is oriented perpendicular to the Figure, and thus appears as a line in those Figures.

In some cases, a viewing angle of 45 degrees is optimal. Determining an optimal viewing angle involves a trade-off of at least three factors. The first factor suggest that the viewing angle should be 90 degrees. But the second and third factors indicate that the viewing angle should be less than 90 degrees. The three factors are:

First, as noted above, each image of a cross-section of the eye captured by a camera is multiplied by a scaling factor proportional to the sine of the viewing angle of the camera for that image. This means that as the viewing angle reduces from 90 degrees to 0 degrees, the image being captured compresses along one dimension, from an unscaled cross-sectional slice all the way down to a line. Since the camera's sensor is made up of discretized pixels, this would lead to loss of information in the capture process as light from different points of the objects finds its way to the same camera pixel. Thus, the closer the viewing angle is to 90 degrees, the greater the scaling factor, and the less information that is lost.

Second, as the viewing angle increases, the positioning margin of error reduces. The positioning margin of error is the margin of error for positioning the object such that it stays in the camera's view. In the case of the eye, a fixation target is able to impose constraints on the placement of the eye in one two dimensions, but the eye is still free to move along the optical axis of the projector.

This means that for a camera placed on-axis (0 degree viewing angle), the margin of error is infinite, since the eye would always be along that axis if the fixation target is in view. For a 90 degree viewing angle, however, the margin of error is proportional to the ratio of the field of view of the camera at that depth to the size of the object. In general, for any viewing angle, the margin of error is proportional to the ratio of the field of view of the camera at that depth to the size of the object scaled by the sine of the viewing angle.

Third, the geometry of the eye imposes practical constraints on the viewing angles that would result in good data capture for reconstruction. The eye is not purely transparent under visible light illumination—the sclera and the iris are opaque. This would make it impossible to view the eye lens at a 90 degree viewing angle, even if the position of the eye could be precisely controlled, because the eye lens would be occluded by the sclera. Thus, it is desirable to have a small enough viewing angle to be able to image the eye lens through the pupil, avoiding occlusion by the sclera and the iris.

In the examples shown in FIGS. 1A, 1D, 2B, 2D, 5B, 5C, a moving straight line of light in the frame of the projector is projected as a moving light sheet. Each orientation of this sheet of light illuminates a different cross-section of the eye.

In illustrative implementations of this invention, a MEMS-driven programmable light source, such as a pico-projector, programmatically controls the orientation of the light sheet without any moving parts.

In many implementations of this invention, a laser pico-projector projects the light pattern. Each individual pixel in the laser pico-projector comprises a collimated beam originating from the laser source within the projector. Thus, the laser pico-projector does not require refocusing for different depths—unlike a conventional LED pico-projector.

Advantageously, a laser pico-projector has a high contrast ratio, which means that the intensity of light projected for dark pixels is many orders of magnitude lower than that for bright pixels. Therefore, if a single thin line of light is projected in the frame of the projector, the resultant beam emitted by the projector very nearly approximates a thin light sheet, with almost no stray illumination from dark pixels. This line may then be moved programmatically in the frame of the projector, to change the orientation of the sheet of light.

In illustrative implementations, a pico-projector (e.g., 101) emits a moving light sheet, by projecting a bright line of light that changes position by illuminating different pixels in the pico-projector.

Scanning the Eye

In illustrative implementations, over the course of each complete scan, a plane of light changes orientations, and thus enters the eye from different angles.

As a result, at each different orientation of the plane of light, a different cross-section of the anterior segment is illuminated by the sheet of light and imaged by the two cameras.

In some implementations, a pico-projector emits light from different pixels of the projector at different times during the course of a complete scan. At any given time, only a single line of pixels in the pico-projector is "on"— that is, emitting light. During each scan, this line of light sweeps across the pico-projector. This in turn causes the pico-projector to emit a moving sheet of light. This moving sheet of light is steered by optical components (e.g., lenses or reflectors) into the eye, such that as the sheet of light moves, it enters the eye at different angles and illuminates different cross-sections of the anterior segment of the eye.

FIGS. 2A, 2B, 2C and 2D show different light patterns projected at different times during a scan, in an illustrative implementation of this invention.

Figure 2B:
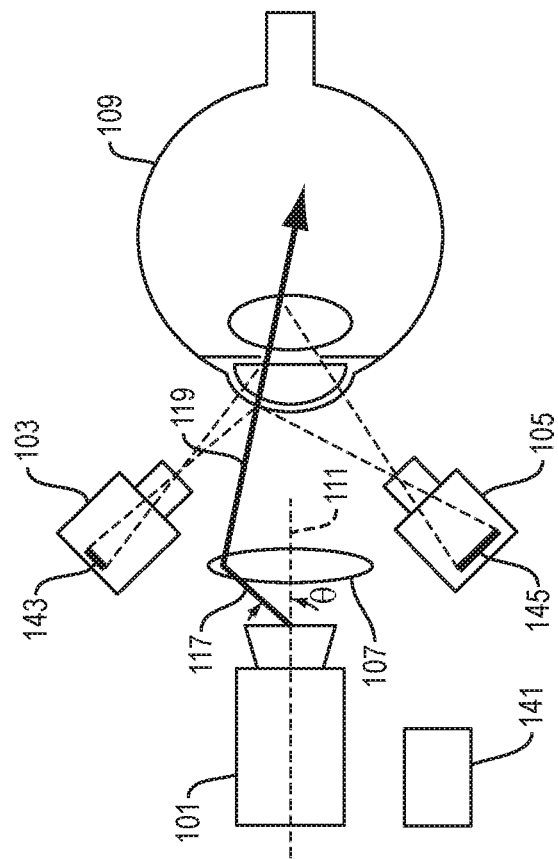
FIG. 2B shows the projector projecting the off-center light while two cameras capture images.
Figure 2A:
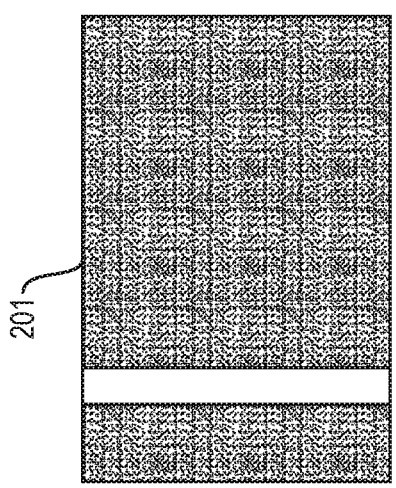
FIG. 2A shows an off-center light pattern 201 displayed by a projector.

FIG. 2A shows an off-center light pattern 201 displayed by the projector. FIG. 2B shows the projector projecting the off-center light pattern while two cameras capture images.

In FIG. 2A, a line of light is off center relative to the center of the projector. In FIG. 2B, the off-center line of light results in a sheet of light 117 exiting the projector 101 at an angle θ relative to the optical axis of the projector 111.

FIG. 2C shows a centered light pattern 203 displayed by a projector. FIG. 2D shows the projector projecting the centered light pattern while two cameras capture images.

In FIG. 2C, a line of light is centered relative to the center of the projector. In FIG. 2D, the centered line of light results in a sheet of light 117 exiting the projector 101 along the optical axis of the projector 111.

The sheet of light is oriented in a different direction in FIG. 2B than in FIG. 2D. Thus, the cross-section imaged by the cameras 103, 105 in FIG. 2B is different than the cross-section imaged by the cameras 103, 105 in FIG. 2D.

Handheld Device

In some embodiments, a handheld device houses the light source, cameras and other optical components. The handheld device is manually held in place against an eye.

Figure 3B:
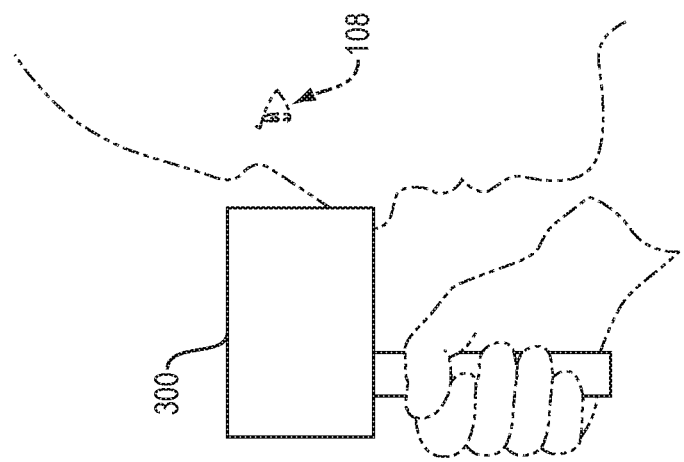
FIG. 3B is a side view of a handheld device for anterior segment imaging.
Figure 3A:
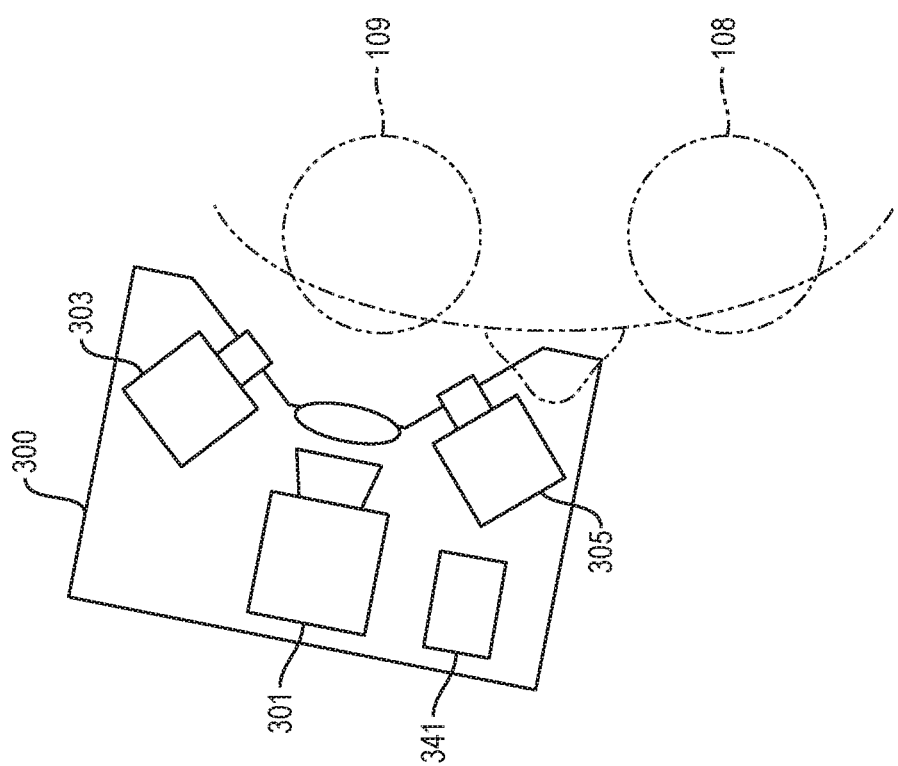
FIG. 3A is a top view of a handheld device for anterior segment imaging.

FIGS. 3A and 3B show a handheld device, in an illustrative implementation of this invention.

FIG. 3A is a top view of a handheld device 300 for anterior segment imaging. The handheld device houses at least a light source 301 (e.g., a laser pico-projector), two cameras 303, 305 and a computer 341. For example, computer 341 may comprise a microprocessor.

FIG. 3B is a side view of the handheld device 300.

A disadvantage of a handheld device is that the handheld device tends to move relative to the subject's head and eye. This unwanted relative motion tends to reduce the accuracy of the reconstruction—e.g., the computation of the 3D shape of the anterior segment of the eye.

Head-Mounted Device

In some embodiments, a head-mounted device ("HMD") houses the light source, cameras and other optical components. For example, the HMD may comprise a helmet, hat or other headwear, or may be attached to straps worn over or around the head.

The motion of the imaging system relative to the user's head is much less in the HMD embodiment than in the handheld embodiment, thereby increasing the accuracy of the reconstruction in the HMD embodiment.

FIGS. 3A and 3B show an HMD, in an illustrative implementation of this invention.

FIG. 4A is a top view of a head-mounted device 400 for anterior segment imaging. The HMD 400 houses at least: (a) a light source 407 and two cameras 403, 405 for imaging the right eye 109; (b) a light source 417 and two cameras 413, 415 for imaging the left eye 108; and (c) a computer 441. For example, computer 441 may comprise a microprocessor.

FIG. 4B shows hardware inside a head-mounted device 400 for anterior segment imaging. A light source 407 (e.g., a pico-projector) emits light that travels though lens 423 and reflects off mirror 421 into right eye 109. Likewise, a light source 417 (e.g., a pico-projector) emits light that travels though lens 433 and reflects off mirror 431 into left eye 108. In FIG. 4B, light exits the light sources 407, 417 in a downward vertical direction, and is reflected by mirrors 421, 431 which are each oriented by an angle of 45 degrees relative to vertical.

Fixation Target

In some implementations, a light source (e.g., a pico-projector) displays a visual fixation target to reduce rotational motion of the eyeball with respect to the imaging system.

Figure 5A:
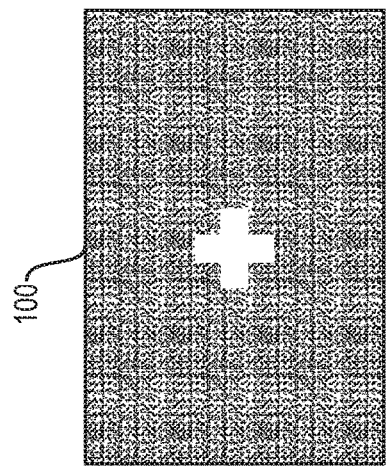
FIG. 5A shows a visual fixation target.
Figure 5C:
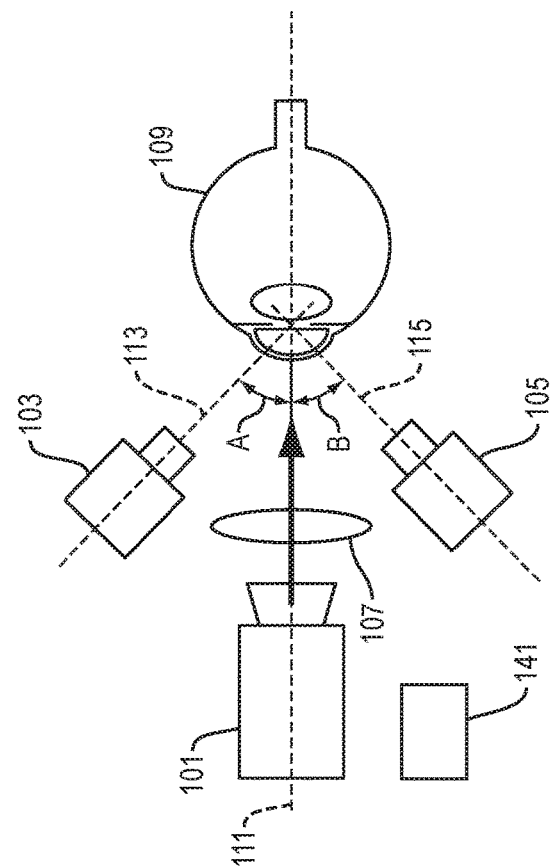
FIG. 5C shows an eye that has rotated, in order to look directly at a visual fixation target displayed by a pico-projector.
Figure 5B:
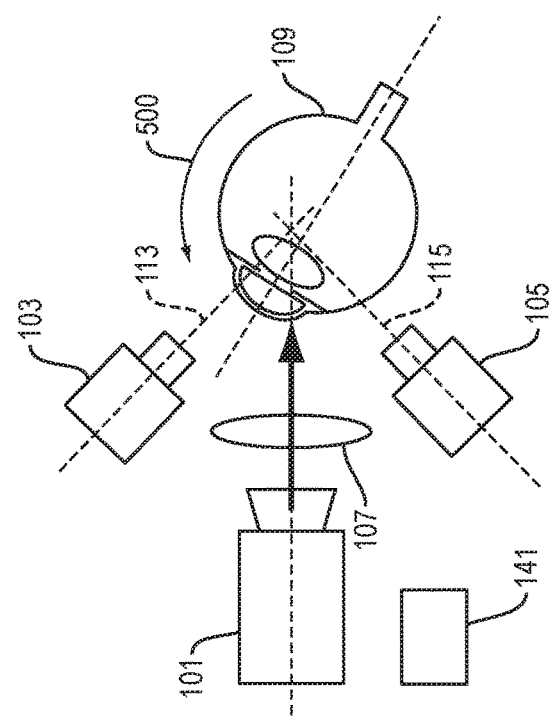
FIG. 5B shows an eye that is not looking directly at a visual fixation target displayed by a pico-projector.

FIGS. 5A, 5B and 5C show an example of using a visual fixation target to align an eye, in an illustrative implementation of this invention.

FIG. 5A shows a visual fixation target 100. The target 100 is visible to the user when optical axis of the pico-projector is well-aligned with the optical axis of the eye, and is not visible otherwise.

FIG. 5B shows an eye 109 that is not looking directly at the visual fixation target displayed by a pico-projector 101. The target is not visible to the user. In order to be able to see the visual fixation target, the eye 109 needs to rotate in rotational direction 500.

FIG. 5C shows an eye that has rotated, in order to look directly at a visual fixation target displayed by a pico-projector. The optical axis of the pico-projector is aligned with the optical axis of the eye, and the fixation target is visible to the user.

In the example shown in FIGS. 5A, 5B and 5C, the visual fixation target is a different color (e.g., red) than the projected sheet of light. The fixation target is projected at the same time as the sheet of light.

In some implementations, the optical axis 113, 115 of each camera 103, 105 is at an angle of 45 degrees relative to the optical axis 111 of the pico-projector 101. Furthermore, in some cases at some times: (a) the optical axis of the eye and the optical axis of the pico-projector are aligned; and thus (b) the optical axis of each camera is at an angle of 45 degrees relative to the optical axis of the eye.

FIG. 5C illustrates this "45 degree" configuration. In the example shown in FIG. 5C: Angle A is the angle between the optical axis 113 of camera 103 and the optical axis 111 of the pico-projector. Likewise, Angle B is the angle between the optical axis 115 of camera 105. Angles A and B are each 45 degrees. In the example shown in FIG. 5C, the eye and pico-projector are optically aligned, such that optical axis of the pico-projector coincides with and is parallel with the optical axis 111 of the pico-projector.

Ellipsoidal Reflector

In some implementations, an ellipsoidal reflector is employed, in order to increase the angular range of the scan and to reduce chromatic aberrations.

Figure 9:
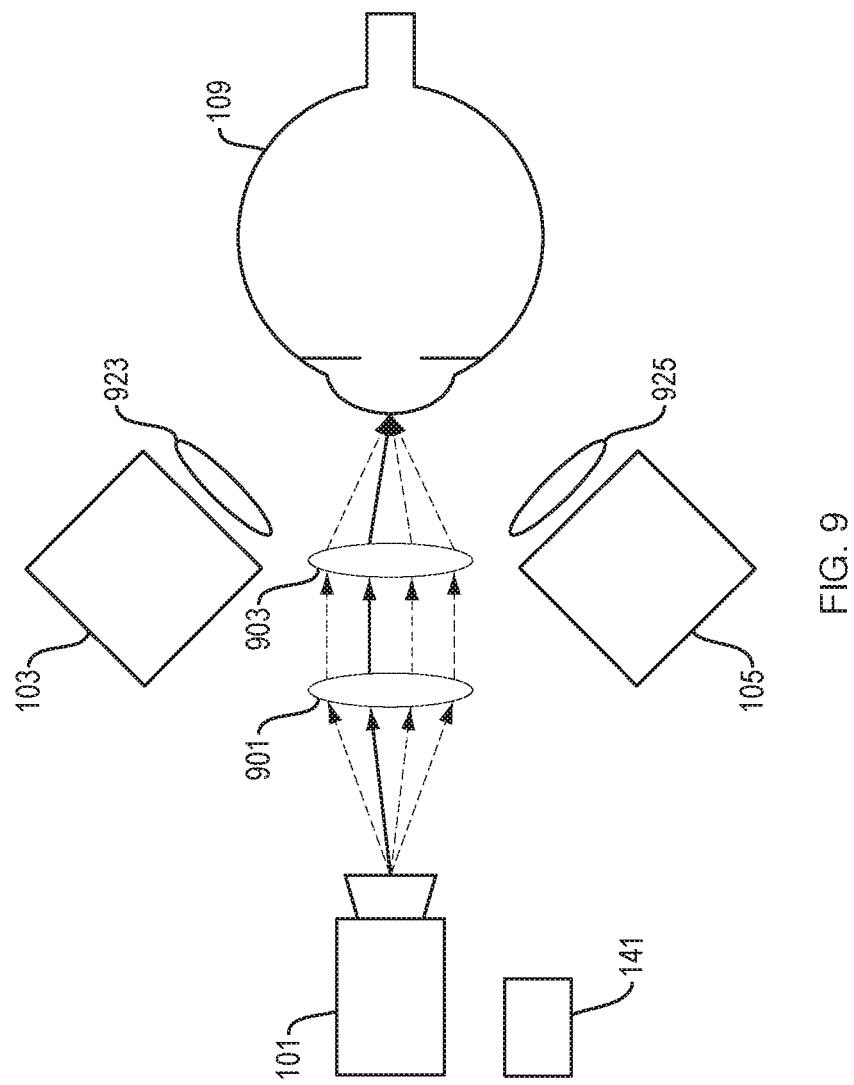
FIG. 9 shows a set of multiple lenses, which includes a collimating lens.

Thus, the ellipsoidal reflector solves two problems associated with a two-lens embodiment of this invention (such as the two lens embodiment with a collimating lens, shown in FIG. 9). These two problems are:

First, chromatic aberration as the light travels through media of refractive index different from that of air (as it travels through the lenses)

Second, the maximum angular range of the scan ("sweep angle") attainable is constrained by the type of lens used. A lens with a high refractive index would allow a higher sweep angle, but would induce more chromatic aberration, while one of a lower refractive index would induce lower chromatic aberration, but would limit the sweep angle attainable. Combination lenses, such as achromatic lenses, may be used to greatly reduce the chromatic aberration, but this usually limits the sweep angle to less than 40 degrees.

Figure 6:
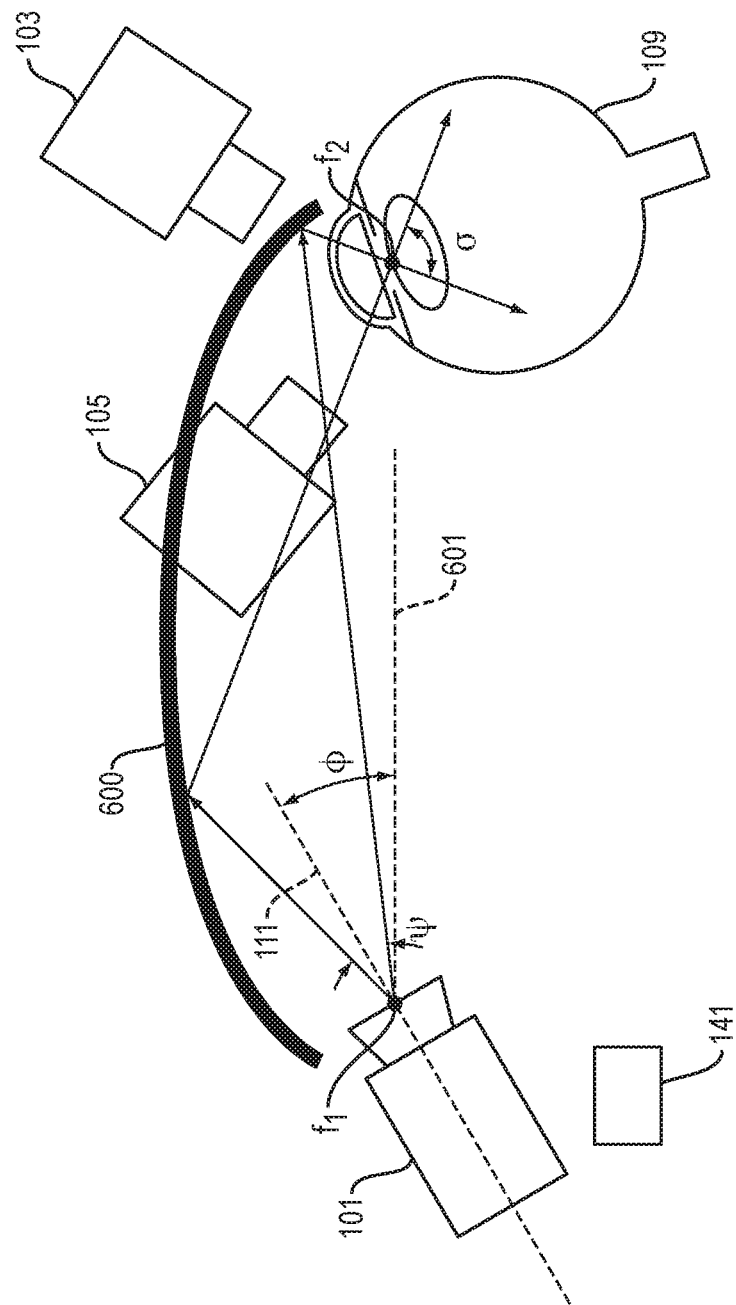
FIG. 6 shows an ellipsoidal reflector.

FIG. 6 shows an ellipsoidal reflector 600, in an illustrative implementation of this invention. The properties of the ellipsoid ensure that all the light emitted from focal point f1 converges at f2, with an angle of convergence that varies with the eccentricity e of the ellipsoid and angle $\phi$. Angle $\phi$ is the angle between the optical axis 111 of pico-projector 101 and the major axis 611 of the ellipsoid. Angle $\psi$ is the angular spread of the beam emitted by the projector.

Placing the eye at f2, as shown in FIG. 6, results in the light sheet rotating about a point f2 within the eye during the course of a complete scan.

In some implementations: (a) the projector is positioned at one focus of the ellipsoid and the eye at the other focus of the ellipsoid; and (b) the angular range of the scan is sweep angle $\sigma$, where $\sigma=f(\psi, e, \phi)$. In some cases, an e and $\phi$ may be selected, for a given $\psi$, such that the sweep angle $\sigma$ is increased. For example, in some cases, the sweep angle $\sigma$ is up to 3-4 larger than the angle $\psi$ (i.e., the angular spread of the beam emitted by the projector).

In the example shown in FIG. 6, because reflection occurs at the surface of the ellipsoidal reflector, and there are no lenses involved, there is little to no chromatic aberration.

Compact Implementation of Ellipsoidal Reflector

A problem with the ellipsoidal configuration shown in FIG. 6 is that, in order to achieve a significant magnification, the ellipsoidal reflector tends to greatly increase the overall dimensions of the imaging system. This is because the projector and eye are placed at different foci along the major axis of the ellipsoid.

In some implementations, this problem is solved by adding a mirror (e.g., a flat mirror) to fold the optical path.

Figure 7:
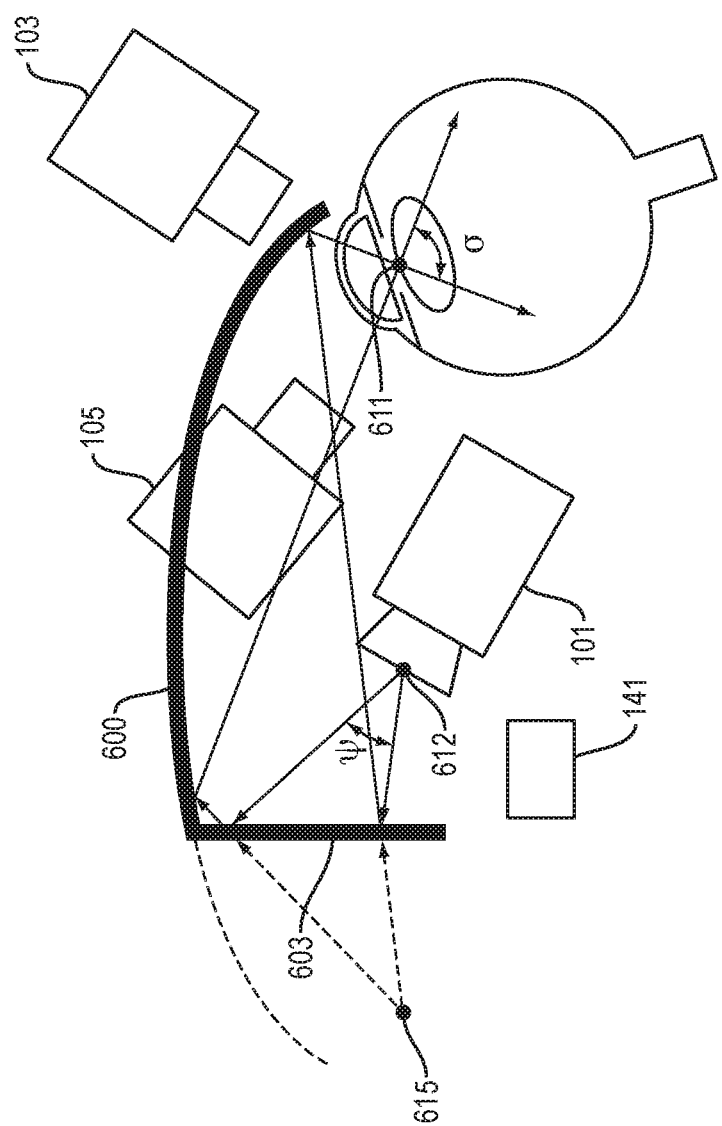
FIG. 7 shows an imaging system with an ellipsoidal reflector and an additional mirror.

FIG. 7 shows an imaging system with an ellipsoidal reflector and an additional mirror, in an illustrative implementation of this invention. In FIG. 7, mirror 603 folds the optical path, thereby allowing a compact form factor.

Specifically, in the example shown in FIG. 7, a mirror 603 causes light to appear to be emitted from point 615, even though the light is actually being emitted by the projector 101 placed at point 612. This is achieved by positioning the mirror 603 and projector 101 such that the virtual image of the projector 101 is at point 615 and thus, the imaging system behaves as though light is emitted by a source at point 615. Points 611 and 615 are foci of the ellipsoidal reflector.

Single Camera

In some cases, a single camera, instead of two or more cameras, is employed. The single camera captures data at two different angles from the optical axis of the projector, by capturing light that reflects off at least two different mirrors.

Figure 8:
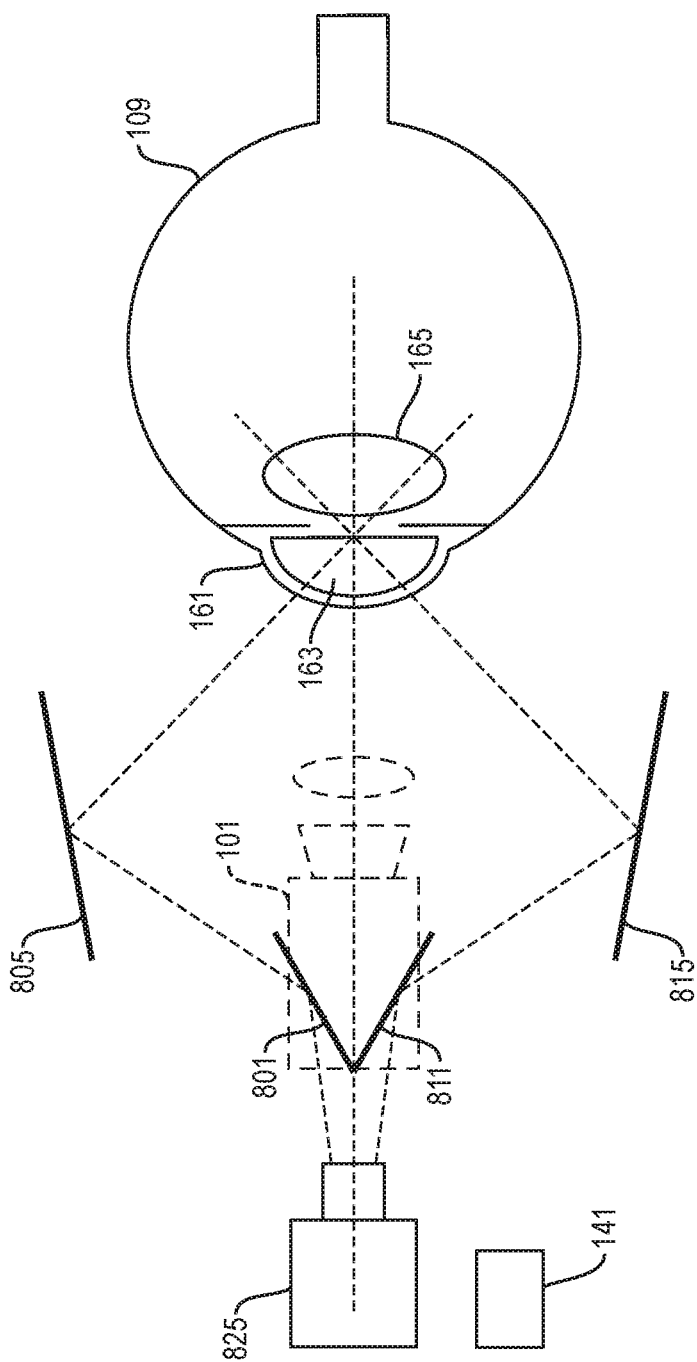
FIG. 8 shows mirrors for capturing images from two different vantage points with a single camera.

FIG. 8 shows mirrors for capturing images from two different vantage points with a single camera, in an illustrative implementation of this invention. In the example shown in FIG. 8, a pico-projector 101 emits light that travels to, and reflects from, an eye 109. A portion of the reflected light travels from the eye 109 to camera 825 by reflecting off mirrors 801 and 805. Another portion of the light travels from the eye 109 to camera 825 by reflecting off mirrors 811 and 815. Thus, camera 825 images the eye 109 from two different vantage points—that is, from the vantage point of mirror 805 and the vantage point of mirror 815. The two data streams (from mirrors 801, 805 on the one hand, and from mirrors 811, 815 on the other hand) are focused onto different regions of the image sensor of camera 825 and are processed separately by one or more computers 141.

Collimating Lens

FIG. 9 shows a set of multiple lenses that includes a collimating lens, in an illustrative implementation of this invention.

Using only a single lens to steer the light sheet emitted by a laser pico-projector suffers from at least two problems: First, pixels of the laser pico-projector are no longer collimated after refraction through the lens. Second, the angle swept by the light sheet on the eye is small.

Is some cases, these problems are solved by using a set of multiple lenses, including a collimating lens, in order to steer light to the eye.

In the example shown in FIG. 9, the lens system that steers light to the eye includes lens 901 and lens 903. Each of these lenses 901, 903 comprises a positive lens that is an achromatic doublet. Lens 901 has a focal length $f_3$. Lens 903 has a focal length $f_4$. These lens are positioned such that: (a) lens 901 is at its focal length $f_3$ from the projector 101; (b) lens 903 is at its focal length $f_4$ from a point in the eye 109, and (c) lens 901 and lens 903 are separated from each other by a distance equal to $f_3+f_4$. Light exiting lens 901 is collimated. Thus, lens 901 collimates the beam emitted by the projector 101 and lens 903 refocuses the beam to a virtual point within the eyeball.

In some cases, employing a set of multiple lenses including a collimating lens: (a) causes each collimated pixel emerging from the projector to produce a collimated pixel at the eyeball, and (b) increases the sweep angle.

In some cases, one or more lenses (e.g., 923, 925) are positioned in an optical path between an eye and a camera.

Reconstruction Algorithm

In illustrative implementations, one or more computers calculated, based on data captured by the one or more cameras, a 3D shape of one or more structures in an anterior segment of an eye.

A wide variety of algorithms may be employed to compute the 3D shape from data captured by the cameras.

Figure 10:
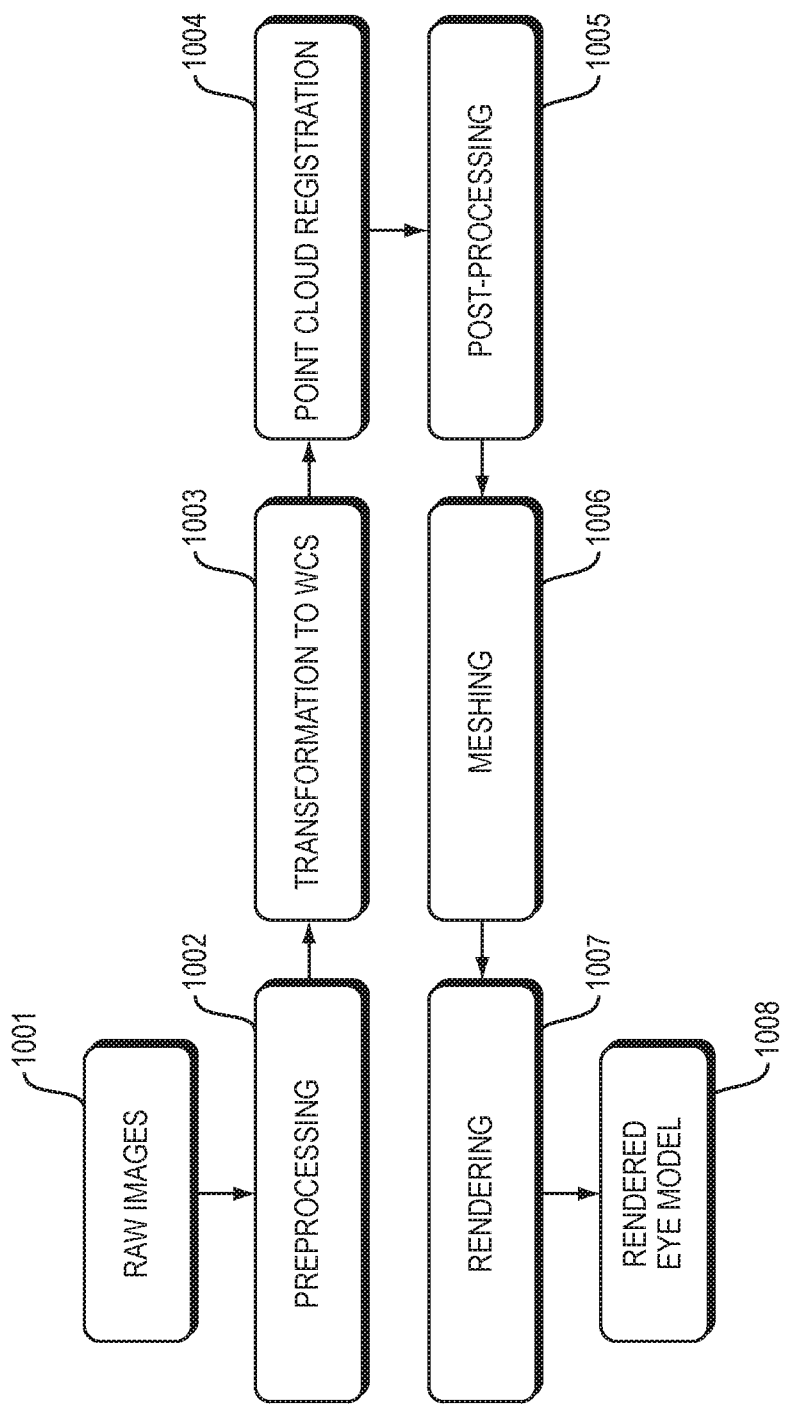
FIG. 10 shows steps in a method for reconstructing 3D shape.

FIG. 10 shows steps in a method for reconstructing 3D shape, in an illustrative implementation of this invention. In the example shown in FIG. 10, the method starts with one or more cameras capturing raw images (Step 1001). The method also includes one or more computers performing the following steps. Preprocessing: The preproccessing step includes noise removal, global and direct illumination separation, thresholding, and brightness/contrast adjustments to clearly bring out the corneal epithelium, corneal endothelium, lens and other structures in the anterior segment of an eye (Step 1002). Transformation to World Coordinate System: In the transformation step, rotations, translations and projection models are applied to transform the cornea from the image plane of the camera to a world coordinate system (WCS). The inverse problem is solved to determine the 3D orientation of the captured cross-section in the actual cornea (Step 1003). Point Cloud Registration: In the point cloud registration step, each camera produces a separate 3D reconstructed surface. These surfaces are registered based on known parameters, such as the angles at which the cameras are placed with respect to the optical axis of the projector, the distance between the cameras, the distance between the cameras and the eye, and the magnification power of focusing optics (Step 1004). Post-processing: In the post-processing step, outliers and specular reflections are removed. The point cloud registration is refined to generate smooth, continuous surfaces (Step 1005). Meshing: In the meshing step, the point cloud is meshed to convert it to a surface for rendering (Step 1006). Rendering: In the rendering step, the meshed surface is rendered under different illumination conditions. For example, in some use scenarios, the rendering simulates illumination in a conventional slit lamp exam with any slit width or orientation. Topographical and curvature maps of the corneal epithelium and endothelium are independently computed and, based on these maps, the cornea thickness is determined at every point (Step 1007). A rendered eye model is outputted (Step 1008).

Reconstruction with Other Light Patterns

Projecting a light sheet simplifies the reconstruction problem, since each image corresponds to a single illuminated plane. However, this invention is not limited to projecting light sheets. Any programmable illumination that projects any light pattern onto the eye may be employed. Here are some non-limiting examples: Other patterns may be used to enhance contrast of certain regions of the eye and better bring out certain features if a patient is suspected to have a particular condition. Projection of different colors on different parts of the eye may single out features based on their scattering properties under different wavelengths. Also, the response of different regions of the eye to certain fluorescent dyes (such as in the fluorescein eye stain test) may be measured, without changing physical filters in the device. Both a light sheet and other programmable illumination may be simultaneously steered onto the eye, to facilitate overlaying of defects and features of interest in high contrast on a reconstructed 3D model.

Prototypes

The following paragraph describes two prototypes. These two prototypes are non-limiting examples of this invention.

In these two prototypes: The pico-projector comprises a PicoPro® laser pico-projector with a 1:3 throw ratio and a contrast ration of 80000:1. The high resolution of the projector allows for 1920 vertical line positions or 720 horizontal line positions, allowing for fine control over the orientation of the light sheet. Two Point Grey® Blackfly color cameras with 1.3 MP sensors image the eye from two directions. At any given time during each scan of the eye, one of the cameras is at a higher viewing angle than the other camera. A computer selects, scales and stores the image captured with the camera with a higher viewing angle, based on the known position of the light sheet. In one prototype, an Edmund Optics® ellipsoidal reflector of 128 mm diameter and 288 mm focal length steers light from the pico-projector to the eye. In the other prototype, a lens system steers light to an eye. The lens system includes two Thorlabs® achromatic doublets with a focal length of 30 mm and a diameter of 1 in, coated for operation in the visible range (400-700 nm).

This invention is not limited to the prototypes described in the preceding paragraph. This invention may be implemented in many other ways.

Computers

In illustrative implementations of this invention, one or more electronic computers (e.g., 141, 341, 441) are programmed and specially adapted: (1) to control or interface with any projector or cameras; (2) to compute any pattern displayed by a pico-projector; (3) to perform algorithms involving reconstruction of 3D shape, including algorithms that include pre-processing of an image, transformation into a world coordinate system, point cloud registration, rendering, meshing, or post-processing; (4) to perform any other calculation, computation, program, algorithm, or computer function described or implied above; (5) to receive signals indicative of human input; (6) to output signals for controlling transducers for outputting information in human perceivable format; and (7) to process data, to perform computations, to execute any algorithm or software, and to control the read or write of data to and from memory devices (items 1-7 of this sentence referred to herein as the "Computer Tasks"). The one or more computers may be in any position or positions within or outside of the imaging system. For example, in some cases (a) at least one computer is housed in or together with other components of the imaging system, such as a pico-projector or camera, and (b) at least one computer is remote from other components of the imaging system. The one or more computers communicate with each other or with other components of the imaging system either: (a) wirelessly, (b) by wired connection, (c) by fiber-optic link, or (d) by a combination of wired, wireless or fiber optic links. For example, computer 141 communicates with projector 101 and cameras 103, 105 either wirelessly, by wired connection, by fiber-optic link, or by a combination of wired, wireless or fiber optic links.

In exemplary implementations, one or more computers are programmed to perform any and all calculations, computations, programs, algorithms, computer functions and computer tasks described or implied above. For example, in some cases: (a) a machine-accessible medium has instructions encoded thereon that specify steps in a software program; and (b) the computer accesses the instructions encoded on the machine-accessible medium, in order to determine steps to execute in the program. In exemplary implementations, the machine-accessible medium comprises a tangible non-transitory medium. In some cases, the machine-accessible medium comprises (a) a memory unit or (b) an auxiliary memory storage device. For example, in some cases, a control unit in a computer fetches the instructions from memory.

In illustrative implementations, one or more computers execute programs according to instructions encoded in one or more tangible, non-transitory, computer-readable media. For example, in some cases, these instructions comprise instructions for a computer to perform any calculation, computation, program, algorithm, or computer function described or implied above. For example, in some cases, instructions encoded in a tangible, non-transitory, computer-accessible medium comprise instructions for a computer to perform the Computer Tasks.

Definitions

The terms "a" and "an", when modifying a noun, do not imply that only one of the noun exists.

"Collimating lens" means a lens that refracts light such that light exiting the lens is collimated.

To compute "based on" specified data means to perform a computation that takes the specified data as an input.

Here are some non-limiting examples of a "camera": (a) a digital camera; (b) a digital grayscale camera; (c) a digital color camera; (d) a video camera; (e) a light sensor or image sensor, (f) a set or array of light sensors or image sensors; (g) an imaging system; (h) a light field camera or plenoptic camera; (i) a time-of-flight camera; and (j) a depth camera. A camera includes any computers or circuits that process data captured by the camera.

To say that X "causes" Y means that X is a direct or indirect cause of Y, and has no implication regarding whether X is the sole cause of Y.

The term "comprise" (and grammatical variations thereof) shall be construed as if followed by "without limitation". If A comprises B, then A includes B and may include other things.

The term "computer" includes any computational device that performs logical and arithmetic operations. For example, in some cases, a "computer" comprises an electronic computational device, such as an integrated circuit, a microprocessor, a mobile computing device, a laptop computer, a tablet computer, a personal computer, or a mainframe computer. In some cases, a "computer" comprises: (a) a central processing unit, (b) an ALU (arithmetic logic unit), (c) a memory unit, and (d) a control unit that controls actions of other components of the computer so that encoded steps of a program are executed in a sequence. In some cases, a "computer" also includes peripheral units including an auxiliary memory storage device (e.g., a disk drive or flash memory), or includes signal processing circuitry. However, a human is not a "computer", as that term is used herein.

"Defined Term" means a term or phrase that is set forth in quotation marks in this Definitions section.

The term "e.g." means for example.

"Elliptical focal point" means a focus of an ellipse, in the geometric sense.

The fact that an "example" or multiple examples of something are given does not imply that they are the only instances of that thing. An example (or a group of examples) is merely a non-exhaustive and non-limiting illustration.

Unless the context clearly indicates otherwise: (1) a phrase that includes "a first" thing and "a second" thing does not imply an order of the two things (or that there are only two of the things); and (2) such a phrase is simply a way of identifying the two things, respectively, so that they each may be referred to later with specificity (e.g., by referring to "the first" thing and "the second" thing later). For example, unless the context clearly indicates otherwise, if an equation has a first term and a second term, then the equation may (or may not) have more than two terms, and the first term may occur before or after the second term in the equation. A phrase that includes a "third" thing, a "fourth" thing and so on shall be construed in like manner.

As used herein, the "foci" and "major axis" of an ellipsoid mean the foci and major axis, respectively, of an ellipse that is a planar cross-section of the ellipsoid, where the cross-section is through the center of the ellipsoid.

"For instance" means for example.

In the context of a camera (or components of the camera), "front" is optically closer to the scene being imaged, and "rear" is optically farther from the scene, during normal operation of the camera. In the context of a display device (or components of the display device), "front" is optically closer to a human viewer, and "rear" is optically farther from the viewer, when the viewer is viewing a display produced by the device during normal operation of the device. The "front" and "rear" of a display device continue to be the front and rear, even when no viewer is present.

"Herein" means in this document, including text, specification, claims, abstract, and drawings.

As used herein: (1) "implementation" means an implementation of this invention; (2) "embodiment" means an embodiment of this invention; (3) "case" means an implementation of this invention; and (4) "use scenario" means a use scenario of this invention.

The term "include" (and grammatical variations thereof) shall be construed as if followed by "without limitation".

"Intensity" means any measure of or related to intensity, energy or power. For example, the "intensity" of light includes any of the following measures: irradiance, spectral irradiance, radiant energy, radiant flux, spectral power, radiant intensity, spectral intensity, radiance, spectral radiance, radiant exitance, radiant emittance, spectral radiant exitance, spectral radiant emittance, radiosity, radiant exposure or radiant energy density.

"Lens" means a single lens, compound lens or set of multiple lenses.

"Light" means electromagnetic radiation of any frequency. For example, "light" includes, among other things, visible light and infrared light. Likewise, any term that directly or indirectly relates to light (e.g., "imaging") shall be construed broadly as applying to electromagnetic radiation of any frequency.

Non-limiting examples of an "optical component" include: (a) a solid or liquid object that reflects light, including any mirror or ellipsoidal reflector; (b) a solid or liquid object that refracts light, including any lens; and (c) a spatial light modulator.

The term "or" is inclusive, not exclusive. For example, A or B is true if A is true, or B is true, or both A or B are true. Also, for example, a calculation of A or B means a calculation of A, or a calculation of B, or a calculation of A and B.

A parenthesis is simply to make text easier to read, by indicating a grouping of words. A parenthesis does not mean that the parenthetical material is optional or may be ignored.

A "scan" means a sweep of a light pattern over an object such that different points in the object are illuminated by the light pattern at different times during the sweep.

As used herein, the term "set" does not include a group with no elements. Mentioning a first set and a second set does not, in and of itself, create any implication regarding whether or not the first and second sets overlap (that is, intersect).

"Some" means one or more.

Spatial light modulator" means a device (i) that transmits light through the device or reflects light from the device, and (ii) that causes a modulation of the intensity, frequency, phase or polarization state of light transmitted through or reflected from the device, such that the modulation depends on the spatial position at which the light is incident on the device.

As used herein, a "subset" of a set consists of less than all of the elements of the set.

To say that a position of X is "substantially constant" relative to Y throughout an entire period means that radial distance $\rho$, polar angle $\theta$, and azimuthal angle $\varphi$ are each substantially constant throughout the entire period. For purposes of the preceding sentence, $\rho$, $\theta$, and $\varphi$ are the coordinates of Y in a spherical coordinate system in which X is at the origin of the coordinate system.

To say that a distance is "substantially constant" throughout an entire period means that the distance has a value that is within a single range, such that, at all times in the entire period: (a) the lowest value in the range is equal to a constant number minus ten percent of the constant number; and (b) the highest value in the range is equal to the constant number plus ten percent of the constant number.

To say that an angle is "substantially constant" throughout an entire period means that the angle has a number of degrees that is within a single range, such that, at all times in the entire period: (a) the lowest value in the range is equal to a constant number minus ten; and (b) the highest value in the range is equal to the constant number plus ten.

The term "such as" means for example.

"3D position" of a set of points means 3D position of the points relative to each other or relative to a coordinate system.

To say that a machine-readable medium is "transitory" means that the medium is a transitory signal, such as an electromagnetic wave.

To say that images are captured "from at least two different vantage points" means that at least a first image is captured from a first vantage point and a second image is captured from a second vantage point, the first and second images being different from each other and the first and second vantage points being different from each other.

Except to the extent that the context clearly requires otherwise, if steps in a method are described herein, then the method includes variations in which: (1) steps in the method occur in any order or sequence, including any order or sequence different than that described; (2) any step or steps in the method occurs more than once; (3) different steps, out of the steps in the method, occur a different number of times during the method, (4) any combination of steps in the method is done in parallel or serially; (5) any step or steps in the method is performed iteratively; (6) a given step in the method is applied to the same thing each time that the given step occurs or is applied to different things each time that the given step occurs; or (7) the method includes other steps, in addition to the steps described.

This Definitions section shall, in all cases, control over and override any other definition of the Defined Terms. For example, the definitions of Defined Terms set forth in this Definitions section override common usage or any external dictionary. If a given term is explicitly or implicitly defined in this document, then that definition shall be controlling, and shall override any definition of the given term arising from any source (e.g., a dictionary or common usage) that is external to this document. If this document provides clarification regarding the meaning of a particular term, then that clarification shall, to the extent applicable, override any definition of the given term arising from any source (e.g., a dictionary or common usage) that is external to this document. To the extent that any term or phrase is defined or clarified herein, such definition or clarification applies to any grammatical variation of such term or phrase, taking into account the difference in grammatical form. For example, the grammatical variations include noun, verb, participle, adjective, and possessive forms, and different declensions, and different tenses. In each case described in this paragraph, the Applicant or Applicants are acting as his, her, its or their own lexicographer.

Variations

This invention may be implemented in many different ways. Here are some non-limiting examples:

In some implementations of this invention, adaptive optics shift focus dynamically during the image capture process. For example, in some cases, the adaptive optics include a fluidic lens. Advantageously, in some cases, these adaptive optics correct for the shallow depth of field associated with large aperture lenses.

In some implementations, this invention is a method comprising a projector and one or more optical components projecting a light pattern that scans at least a portion of an anterior segment of an eye of a user while one or more cameras capture images of the anterior segment, such that: (a) during each scan, different parts of the projector emit light at different times, causing the light pattern to repeatedly change orientation relative to the eye and thus to illuminate multiple different cross-sections of the anterior segment; (b) the one or more cameras capture images of each cross-section from a total of at least two different vantage points relative to the head of the user; and (c) the position of the one or more cameras, the projector and the one or more other optical components relative to the head of the user remains substantially constant throughout each entire scan. In some cases, the one or more optical components include an ellipsoidal reflector. In some cases: (a) a surface of the reflector comprises a surface of an ellipsoid; (b) a planar cross-section of the ellipsoid is an ellipse that has a first elliptical focal point and a second elliptical focal point; and (c) the first elliptical focal point coincides with a point in the pico-projector and the second elliptical focal point coincides with a point in the anterior segment. In some cases: (a) the one or more optical components also include an additional mirror; and (b) the additional mirror is positioned such that the mirror produces a virtual image of the projector and folds an optical path from the projector to the anterior segment. In some cases, the one or more optical components comprise a set of multiple lens that together comprise a positive lens. In some cases, at least one lens in the set of multiple lenses comprises a collimating lens. In some cases, the light pattern is a plane of light. In some cases: (a) the one or more cameras comprise a first camera and a second camera; and (b) the two vantage points comprise the position of the first camera and of the second camera, respectively, relative to the head of the user. In some cases: (a) the one or more cameras comprise only a single camera; and (b) the two vantage points comprise the position of a first mirror and of a second mirror, respectively, relative to the head of the user. In some cases, one or more computers calculate, based on the images, 3D position of a set of multiple points in the anterior segment. Each of the cases described above in this paragraph is an example of the method described in the first sentence of this paragraph, and is also an example of an embodiment of this invention that may be combined with other embodiments of this invention.

In some implementations, this invention is an apparatus comprising: (a) a projector and one or more optical components for projecting a light pattern that scans at least a portion of an eye of a user, such that (i) during each scan, different parts of the projector emit light at different times, causing the light pattern to repeatedly change orientation relative to the eye and thus to illuminate multiple different cross-sections of the eye, and (ii) the position of the one or more cameras, the projector and the one or more other optical components relative to the head of the user remains substantially constant throughout each entire scan; and (b) one or more cameras for capturing images of each cross-section from a total of at least two different vantage points relative to the head of the user. In some cases, the one or more optical components include an ellipsoidal reflector. In some cases: (a) a surface of the reflector comprises a surface of an ellipsoid; (b) a planar cross-section of the ellipsoid is an ellipse that has a first elliptical focal point and a second elliptical focal point; and (c) the first elliptical focal point coincides with a point in the pico-projector and the second elliptical focal point coincides with a point in the eye. In some cases: (a) the one or more optical components also include an additional mirror; and (b) the additional mirror is positioned such that the mirror produces a virtual image of the projector and folds an optical path from the projector to the eye. In some cases, the one or more optical components comprise a set of multiple lens that together comprise a positive lens. In some cases, at least one lens in the set of multiple lenses comprises a collimating lens. In some cases, the light pattern is a plane of light. In some cases: (a) the one or more cameras comprise a first camera and a second camera; and (b) the two vantage points comprise the position of the first camera and of the second camera, respectively, relative to the head of the user. In some cases: (a) the one or more cameras comprise only a single camera; and (b) the two vantage points comprise the position of a first mirror and of a second mirror, respectively, relative to the head of the user. In some cases, the apparatus further comprises one or more computers that are programmed to calculate, based on the images, 3D position of a set of multiple points in the eye. Each of the cases described above in this paragraph is an example of the apparatus described in the first sentence of this paragraph, and is also an example of an embodiment of this invention that may be combined with other embodiments of this invention.

The above description (including without limitation any attached drawings and figures) describes illustrative implementations of the invention. However, the invention may be implemented in other ways. The methods and apparatus which are described above are merely illustrative applications of the principles of the invention. Other arrangements, methods, modifications, and substitutions by one of ordinary skill in the art are therefore also within the scope of the present invention. Numerous modifications may be made by those skilled in the art without departing from the scope of the invention. Also, this invention includes without limitation each combination and permutation of one or more of the abovementioned implementations, embodiments and features.

What is claimed is:

1. A method comprising a projector and one or more optical components projecting a light pattern that scans at least a portion of an anterior segment of an eye of a user while one or more cameras capture images of the anterior segment, wherein:
   (a) during each scan, a temporal sequence of emission occurs in the projector, which sequence
      (i) comprises different pixels of the projector emitting light at different times, in such a way that only a subset of the pixels emit light at any given time and which pixels are in the subset changes over time, and
      (ii) causes the light pattern to repeatedly change orientation relative to the eye, in such a way that the light pattern illuminates a set of multiple cross-sections of the anterior segment, each cross-section in the set occurring at a different time than, and being at a different orientation relative to the eye as a whole than, any other cross-section in the set;
   (b) during each scan, the one or more cameras capture images of each cross-section in the set from a total of at least two different vantage points relative to the head of the user;
   (c) throughout each entire scan, the one or more cameras, the projector and the one or more optical components remain in a fixed position relative to each other without moving relative to each other; and
   (d) the one or more optical components include all optical components that steer, to the eye, light which has been emitted by the projector.

2. The method of claim 1, wherein the one or more optical components include an ellipsoidal reflector positioned in such a way that light from the projector reflects from the elliptical reflector and travels to the anterior segment.

3. The method of claim 2, wherein:
   (a) a surface of the reflector comprises a surface of an ellipsoid;
   (b) a planar cross-section of the ellipsoid is an ellipse that has a first elliptical focal point and a second elliptical focal point; and
   (c) the first elliptical focal point is located at a point in the projector and the second elliptical focal point is located at a point in the anterior segment.

4. The method of claim 2, wherein:
   (a) the one or more optical components also include an additional mirror; and
   (b) the additional mirror is positioned in such a way that the mirror produces a virtual image of the projector and folds an optical path, in such a way that light travels from the projector to the mirror, then from the mirror to the ellipsoidal reflector, and then from the ellipsoidal reflector to the anterior segment.

5. The method of claim 4, wherein
   (a) a surface of the reflector comprises a surface of an ellipsoid;
   (b) a planar cross-section of the ellipsoid is an ellipse that has a first elliptical focal point and a second elliptical focal point; and
   (c) the first elliptical focal point is located at a point in the virtual image of the projector and the second elliptical focal point is located at point in the anterior segment.

6. The method of claim 5, wherein the one or more optical elements include a collimating lens.

7. The method of claim 1, wherein the light pattern is a plane of light.

8. The method of claim 1, wherein:
   (a) the one or more cameras comprise a first camera and a second camera; and (b) the two vantage points comprise the position of the first camera and of the second camera, respectively, relative to the head of the user.

9. The method of claim 1, wherein:
(a) the one or more cameras consist of only a single camera; and
(b) the two vantage points comprise the position of a first mirror and of a second mirror, respectively, relative to the head of the user.

10. The method of claim 1, wherein one or more computers calculate, based on the images, 3D position of a set of multiple points in the anterior segment.

11. Apparatus comprising:
(a) a projector and one or more optical elements;
(b) one or more cameras; and
(c) one or more computers;
wherein
(i) the one or more computers are programmed to control the projector and one or more cameras, in such a way that
   (A) the projector and one or more optical components project a light pattern that scans at least a portion of an eye of a user,
   (B) during each scan, a temporal sequence of emission occurs in the projector, which sequence
      (I) comprises different pixels of the projector emitting light at different times, in such a way that only a subset of the pixels emit light at any given time and which pixels are in the subset changes over time, and
      (II) causes the light pattern to repeatedly change orientation relative to the eye, in such a way that the light pattern illuminates a set of multiple cross-sections of the eye, each cross-section in the set being illuminated at a different time, and being at a different orientation relative to the eye as a whole, than any other cross-section in the set, and
   (C) during each scan, the one or more cameras capture images of each cross-section in the set from a total of at least two different vantage points relative to the head of the user,
(ii) throughout each entire scan, the one or more cameras, the projector and the one or more optical components are configured to remain in a fixed position relative to each other without moving relative to each other, and
(iii) the one or more optical components include all optical components of the apparatus that are configured to steer, to the eye, light which has been emitted by the projector.

12. The apparatus of claim 11, wherein the one or more optical components include an ellipsoidal reflector positioned in such a way such that light from the projector reflects from the elliptical reflector and travels to the eye.

13. The apparatus of claim 12, wherein:
(a) a surface of the reflector comprises a surface of an ellipsoid;
(b) a planar cross-section of the ellipsoid is an ellipse that has a first elliptical focal point and a second elliptical focal point; and
(c) the first elliptical focal point is located at a point in the projector and the second elliptical focal point is located at a point in the eye.

14. The apparatus of claim 12, wherein:
(a) the one or more optical components also include an additional mirror; and
(b) the additional mirror is positioned in such a way that the mirror produces (i) a virtual image of the projector and (ii) a folded optical path from the projector to the mirror, then from the mirror to the ellipsoidal reflector, and then from the ellipsoidal reflector to the eye.

15. The apparatus of claim 14, wherein
(a) a surface of the reflector comprises a surface of an ellipsoid;
(b) a planar cross-section of the ellipsoid is an ellipse that has a first elliptical focal point and a second elliptical focal point; and
(c) the first elliptical focal point is located at a point in the virtual image of the projector and the second elliptical focal point is located at point in the eye.

16. The apparatus of claim 15, wherein the one or more optical elements include a collimating lens.

17. The apparatus of claim 11, wherein the light pattern is a plane of light.

18. The apparatus of claim 11, wherein:
(a) the one or more cameras comprise a first camera and a second camera; and
(b) the two vantage points comprise the position of the first camera and of the second camera, respectively, relative to the head of the user.

19. The apparatus of claim 11, wherein:
(a) the one or more cameras consist of only a single camera; and
(b) the two vantage points comprise the position of a first mirror and of a second mirror, respectively, relative to the head of the user.

20. The apparatus of claim 11, wherein the one or more computers are programmed to calculate, based on the images, 3D position of a set of multiple points in the eye.

* * * * *